United States Patent [19]

Greco et al.

[11] Patent Number: 4,879,135

[45] Date of Patent: * Nov. 7, 1989

[54] DRUG BONDED PROSTHESIS AND PROCESS FOR PRODUCING SAME

[75] Inventors: Ralph S. Greco, Princeton; Richard A. Harvey, East Brunswick; Stanley Z. Trooskin, North Brunswick, all of N.J.

[73] Assignee: University of Medicine and Dentistry of New Jersey, Newark, N.J.

[*] Notice: The portion of the term of this patent subsequent to Apr. 26, 2005 has been disclaimed.

[21] Appl. No.: 220,503

[22] Filed: Jul. 18, 1988

Related U.S. Application Data

[63] Continuation-in-part of Ser. No. 852,849, Apr. 11, 1986, which is a continuation-in-part of Ser. No. 633,615, Jul. 23, 1984, Pat. No. 4,740,382.

[51] Int. Cl.$^4$ .......................... A61F 1/00; A61F 1/24
[52] U.S. Cl. .................................. 427/2; 128/334 R; 623/1; 623/11; 623/12; 623/66; 521/30
[58] Field of Search .................... 427/2; 128/334 R; 623/1, 12, 11, 66; 521/30

[56] References Cited

U.S. PATENT DOCUMENTS

| | | | |
|---|---|---|---|
| 4,563,485 | 1/1986 | Fox, Jr. et al. | 523/113 |
| 4,581,028 | 4/1986 | Fox, Jr. et al. | 523/2 |
| 4,612,337 | 9/1986 | Fox, Jr. et al. | 523/113 |
| 4,740,382 | 4/1988 | Greco et al. | 427/2 |

OTHER PUBLICATIONS

Jagpal, R., Greco, R. S.; "Studies of a Graphite-Benzalkoniumoxacillin Surface", Amer. Surg. 45:774-779, 1979.

Greco, R. S., Harvey, R. A., Henry, R., Prahlad, A.: "Prevention of Graft Infection by Antibiotic Bonding," Surg. Forum XXXI: 29-30, 1980.

Henry, R., Harvey, R. A., Greco, R. S.: "Antibiotic Bonding to Vascular Prostheses", J. Thorac. Cardiov. Surg. 82:272-277, 1981.

Harvey, R. A., Greco, R. S.: "The Non-Covalent Bonding of Antibiotics to a Polytetrafluoroethylene Graft", Ann. Surg. 194:642-647, 1981.

Prahlad, A., Harvey, R. A., Greco, R. S.: "Diffusion of Antibiotics from a Polytetrafluoroethylene (PTFE) Surface", Amer. Surg. 47:515-518, 1981.

Greco, R. S., Harvey, R. A.: "The Role of Antibiotic Bonding in the Prevention of Vascular Prosthetic Infections", Ann. Surg. 195:168-171, 1982.

Harvey, R. A., Alcid, D. V., Greco, R. S.: "Antibiotic Bonding to Polytetrafluoroethylene with Tridodecylmethylammonium Chloride", Surg. 92:504-512, 1982.

Greco, R. S., Harvey, R. A., Smilow, P. C., Tesoriero, J. V.: "Prevention of Vascular Prosthetic Infection by a Benzalkoniumoxacillin Bonded Polytetrafluoroethylene Graft", Surg. Gynec. Obstet. 155:28-32, 1982.

Trooskin, S. Z., Harvey, R. A., Greco, R. S.: "Prevention of Catheter Sepsis by Antibiotic Bonding", Surg. Forum 34:132-133, 1983.

Greco, R. S., Tesoriero, J. V., Smilow, P. C., Harvey, R. A.: "Light and Electron Microscopic Studies of an Antibiotic Bonded Vascular Graft", J. Cardiov. Surg. 25:489-497, 1984.

Harvey, R. A., Tesoriero, J. V., Greco, R. S.: "The Non-Covalent Bonding of Penicillin and Cefazolin to Dacron", Amer. J. Surg. 147:205-209, 1984.

Greco, R. S., Harvey, R. A.: "The Biochemical Bonding of Cefoxitin to a Microporous Polytetrafluorethylene Surface", J. Surg. Res. 36A:237-243, 1984.

Donetz, A. P., Harvey, R. A., Greco, R. S.: "The Stability of Antibiotics Bound to Polytetrafluoroethylene with Cationic Surfactants", J. Clin. Microbiol. 19:1-3, 1984.

Greco, R. S., Donetz, A. P., Harvey, R. A.: "The Application of Antibiotic Bonding to the Treatment of Established Vacular Prosthetic Infection", Arch. Surg. 120(1):71-75, 1985.

Trooskin, S. Z., Donetz, A. P., Harvey, R. A., Greco, R. S.: "Prevention of Catheter Sepsis by Antibiotic Bonding", Surgery May 97(5) 547-551, 1985.

Trooskin, S. Z., Harvey, R. A., Greco, R. S., Donetz, A. P.: "Antibiotic Bonded Chronic Peritoneal Dialysis Catheters", Europ. Surg. Res.; Clin. Exper. Surg. XX Congress Europ. Soc.Surg. Res.; Rotterdam, The Netherlands, p. 2, May 1985.

Trooskin, S. Z., Harvey, R. A., Donetz, A. P., Baxter, J., Greco, R. S.: "Infection Resistant Continuous Peritoneal Dialysis Catheters", Nephron (In Press).

Trooskin, S. Z., Harvey, R. A., Donetz, A. P., Greco, R. S.: "Application of Antibiotic Bonding to CAPD Catheters", Frontiers in Peritoneal Dialysis 157-160, 1986.

Trooskin, S. Z. Harvey, R. A., Kahn, M., Lennard, T. W. J., Greco, R. S.: "Results of a Prospective Clinical Trial of Antibiotic Bonded Catheters for Continuous Ambulatory Peritoneal Dialysis (CAPD)".

Harvey, R. A., Greco, R. S.: "Antibiotic Bonding to Vascular Prostheses", Federation Proceedings 41:1556, 1982.

Harvey, R. A., Greco, R. S., Trooskin, S. Z.: "The Binding of Encapsulated Drugs to the Surface of Prostheses", International Biomedical Engineering (In Press).

(List continued on next page.)

*Primary Examiner*—John Kight
*Assistant Examiner*—M. L. Moore
*Attorney, Agent, or Firm*—Klauber & Jackson

[57] ABSTRACT

There is disclosed an improved prosthesis coated, respectively, with an anionic surfactant, a drug such as an antibiotic and/or antithrombotic agent. Optionally, the coated prosthesis may be treated with an ion exchange compound, to remove un-drug bound anionic surfactant. The drug is bound directly to the surfactant coated prosthesis.

17 Claims, No Drawings

OTHER PUBLICATIONS

Crowley, J. P. et als., "Development of Blood-Compatible Materials: Heparinized Surfaces and Platelet Protective Agents", Natl. Heart Lung Inst., N.T.I.S. PB-251 712, Mar., 1976.

Grode, G. A. et als., "A Toxicological Evaluation of Certain Heparin-Quaternary Ammonium Complexes", Natl. Heart Lung Inst., N.T.I.S., PB-226 886, Dec., 1973.

Crowley, J. P. et al., "Development of Blood-Compatible Materials: Heparinized Surfaces and Platelet Protective Agents", Natl. Heart Lung Inst., N.T.I.S., PB-238 763, Dec. 1, 1974.

DRUG BONDED PROSTHESIS AND PROCESS FOR PRODUCING SAME

BACKGROUND OF THE INVENTION

This invention was in part made with Government support under Grant HL 24252 awarded by the National Institutes of Health. The Government has certain rights in this invention.

RELATED APPLICATIONS

This is a Continuation-In-Part application of U.S. Application Ser. No. 0852,849, filed Apr. 11, 1986, which is a Continuation-In-Part of U.S. Application Ser. No. 0633,615, filed July 23, 1984, now U.S. Pat. No. 4,740,382, issued Apr. 26, 1988.

FIELD OF THE INVENTION

This invention relates to methodology for the surface modification of surgical implants permitting the binding of drugs which, after implantation, are slowly released. More particularly, this invention relates to improved surgical implants having sustained, localized delivery of pharmacological agents such as extended antibiotic activity or reduced thrombogenicity, and methods for producing same.

DESCRIPTION OF THE PRIOR ART

The surface modification of surgical implants by the adhesion thereto of pharmacological agents for the purpose of minimizing infection and prosthesis rejection is well-known and has generated broad interest for some time. Many different approaches have been taken including those disclosed in U.S. Pat. No. 4,563,485, U.S. Pat. No. 4,581,028 and U.S. Pat. No. 4,612,337 to Fox, Jr. et al. In these patents, the approach taken has been to attempt to bond an antibiotic or like material directly to a substrate which would then serve as an implant. In each instance, various metal salts of the antibiotics were utilized and other devices for adhesion pursued.

In an abstract presented in November 1979 to the Association for Academic Surgery, there is disclosed the bonding of oxacillin to a polytetrafluoroethylene surface coated with benzalkonium chloride for protection against infection by the device as a result of surgical implantation.

In U.S. Pat. No. 4,442,133 issued Apr. 10, 1984, there is disclosed a process for coating vascular prostheses with a cationic surfactant, such as tridodecylmethyl ammonium chloride (TDMAC), to increase sites for antibiotic bonding, and then prior to utilizatin, the thus coated vascular prostheses are placed in an antibiotic solution to bond the antibiotic thereto. Such antibiotic bonded vascular prostheses exhibit resistance to infection.

The '133 patent pursued the concept initially developed by the inventors Greco, Harvey and Trooskin herein that a positively charged surfactant could be applied to the surface of a prosthesis and that thereafter a negatively charged antibiotic could be similarly applied and bound thereto. This concept was further refined in U.S. Pat. No. 4,740,382, the disclosure of which is incorporated herein by reference, wherein all of the inventors herein determined that subsequent treatment of the thus coated prosthesis with a cationic exchange compound would result in certain improvements in the bonding of the antibiotic to the surfactant and correspondingly, to the surface of the prosthesis.

Further development of the concept to include the scope of the present invention was set forth in parent Application Ser. No. 852,849, filed Apr. 11, 1986. In this Application, anionic surfactants and correspondingly positively charged antibiotics were disclosed, as for the first time they had been experimented with and found to be viable. The present Application is therefore an effort to further disclose and particularize this aspect of the invention, i.e., the development of the antibiotic bonded prosthesis utilizing an anionic surfactant and the oppositely charge drug, antibiotic or other agent or factor.

Applicants are aware of prior art with respect to this area, and in particular, the publications of which they are co-authors.

Thus, in Jagpal et al. *Studies of a Graphite-Benzalkonium-Oxacillin Surface,* AMER. SURG. 45:774–779 (1979), initial discussion of the phenomenon of binding an antibiotic to a surface by use of a cationic detergent was disclosed. The detergent in question, benzalkonium, was shown to have the ability to releasably bind the antibiotic oxacillin. These were the only materials with with the inventors experiments, and was later distinguished in the disclosure of U.S. Pat. No. 4,442,133.

Similarly, in Greco et al., *Prevention of Graft Infection by Antibiotic Bonding,* SURG. FORUM XXXI:29–30 (1980), the authors prepared vascular grafts from polytetrafluoroethylene, which were coated with benzalkonium chloride and oxacillin. These further studies were cumulative with the findings of the 1979 study and were likewise distinguished by the stated U.S. Patent.

In Henry et al., *Antibiotic Bonding to Vascular Prostheses,* J. THORAC. CARDIOV. SURG. 82:272–277 (1981); Harvey et al., The Non Covalent Bonding of Antibiotics to a Polytetrafluoroethylene-Benzalkonium Graft, ANN. SURG. 194:642–647 (1981); Prahlad et al., Diffusion of Antibiotics from a Polytetrafluoroethylene (PTFE) Surface, AMER. SURG. 47:515–518 (1981); and in Greco et al., *The Role of Antibiotic Bonding in the Prevention of Vascular Prosthetic Infections,* ANN. SURG. 195:168–171 (1982), the authors further explored the benzalkonium-oxacillin system and determined some of its parameters of operation. It was not until the filing of the '133 patent that work was done with TDMAC. This work is also reflected in an article published after the filing of the '133 patent, by Harvey et al. entitled *Antibiotic Bonding to Polytetrafluoroethylene with Tridodecylmethyl ammonium chloride* SURG. 92:504–512 (1982).

The remainder of the articles presented further data in corroboration of the principles earlier outlined and are therefore cumulative in their disclosure. All of the articles are concerned with bonding systems in which cationic surfactants are present, and offer no suggestion of the pursuit of a system wherein anionic surfactants may be used in conjunction with oppositely charged antibiotics or the like.

Applicants are also aware of publications by the U.S. Department of Commerce National Technical Information Service having numbers PB-226 886, PB-238 763, and PB-251 712 prepared by Columbus Laboratories and published 1973-1976. These works sought to develop prosthetic vascular materials which are compatible with the body's hematological system. They describe the preparation, biocompatibility and toxicology of a variety of test surfaces, including material containing a complex of TDMAC and heparin. These disclosures in and of themselves are peripheral to the present invention and to the system with which it is concerned, so that the present invention is considered clearly patentable thereover.

OBJECTS OF THE INVENTION

An object of the present invention is to provide improved surfactant-modified implantable devices having a drug, including antibiotics, antithrombogenic agents, thrombolytic agents, disinfectants, etc., bound to the surface thereof.

Yet another objec tof the present invention is to provide an improved implantable device having a drug bonded in such a way as to substantially eliminate thrombosis of said implant.

Another object of the present invention is to provide an improved implantable device having a drug bound thereto of improved release times.

SUMMARY OF THE INVENTION

These and other objects of the present invention are achieved by a prosthesis coated, respectively, with an anionic surfactant and a drug, such as an antibiotic, antithrombotic agent and/or a thrombolytic enzyme. The drug is bound directly to the surfactant-coated prothesis.

DEFINITION OF TERMS

The term "prosthesis" employed herein and through out the present specification and claims is intended to include:
intravenous, peritoneal dialysis, parenteral and urological catheters;
vascular grafts;
ventricular and peritoneovenous shunts;
penile prostheses;
heart valves;
orthopedic prostheses (including hip and knee replacements);
intraocular prostheses (including lenses and cornea);
sutures
prostheses used in reconstructive plastic surgery These device are well known and have been described heretofore for various purposes, including intravenous feeding, peritoneal dialysis, reconstruction of arteries and veins, orthopedic repair, in addition to other uses. These devices will consist of organic polymers and/or metallic materials including:
dacron
nylon
polyacrylamide
polycarbonate
polyethylene
polyformaldehyde
polyglycolic acid
polylactic acid
polymethylmethacrylate
polypropylene
polystyrene
polytetrafluoroethylene
polytrifluorochlorethylene
polyvinylchloride
polyurethane
elastomeric organosilicon polymers, such as polysiloxanes, eg. Silastic ®
cobalt-chromium alloys
stainless steel
titanium.

The term "surfactant" as employed herein and throughout the present specification and claims is intended to include anionic compounds with surface-active properties. These materials are well known and have been described heretofore for various purposes, including wetting, penetrating, emulsifying, dispersing and solubilizing, in addition to other uses. The anionic surfactants are composed of a negatively-charged organic anion and a positively charged counter-ion which is necessary to maintain electrical neutrality; a typical positively-charged counter-ion is a sodium ion, Na+. Coatings of anionic surfactants can exchange their Na+ counter-ion for a positively charged drug, resulting in retention of the pharmacological agent.

The anionic surfactants may be divided into the following major classes:
Alkyl aryl sulfonates
Alkyl sulfates
Alkyl sulfonates
Sulfated and sulfonated amines
Sultated and sulfonated esters and ethers
Esters of phosphoric acid.

Specific examples from this group of anionic surfactants are the following:
Dicetyl phosphate, sodium salt
Dioctadecyl phosphate, sodium salt
Disodium bis(sulfonaphthyl)-methane
Polyoxyethylene sorbitan monostearate
Sodium bis (tridecyl)-sulfosuccinate
Sodium N-methyl-N-methyl-n-oleoyl taurate
Sodium lauryl sulfate
Sodium octylphenoxy polyglycol sulfonate
Sodium alkylbenzenesulfonate
Sodium isopropylnaphthalenesulfonate
Sodium heptadecyl sulfate
Sodium taurocholate
Sodium phosphatidate and derivatives
Sodium hexadecyl sulfonate.

Drugs marked with a "*" are positively charged at physiological pH and thus bind to negatively-charged surfactant coatings.

The term "drug" employed herein and throughout the present specification and claims is intended to include those which are listed below as well as other therapeutic agents known and used for the treatment of human disorders. These compounds are well known and have been described heretofore for various purposes, including the intravenous administration for the prevention of infection, prevention of thrombus formation, the lysis of blood clots, and the modification of tissue reactions to the implanted device.

ANTIBIOTICS aminoglycoside*
amphotericin
ampicillin
carbenicillin
cefazolin
cephalosporin
chloroamphenicol
cylindamycin*
erythromycin
gentamicin*
griseofulvin
kanamycin*
methicillin
nafcillin novobiocin
penicillin
polymyxin
rifampin
streptomycin*
sulfamethoaxozole
sulfonamide
tetracycline*
tobramycin*
trimethoprim
vancomycin.

ANTI-THROMBOTIC DRUGS INCLUDING acetylsalicylic acid (aspirin)
dipyridamole
heparin
ibuprofen
indomethacin
prostaglandins
sulfinpyrazone
warfarin.

THROMBOLYTIC ENZYMES streptokinase
urokinase
plasminogen activator.

DETAILED DESCRIPTION OF THE INVENTION

To facilitate an understanding of the present invention, the present invention will be described with reference to the treatment of a vascular prosthesis prepared from thermoplastic substrates, such as polytetrafluoroethylene, dacron, polyethylene, Silastic ® and the like, although it will be understood by one skilled in the art that the present invention relates to the treatment of any implantable device formed from such materials, e.g.. catheters, heart valves, orthopedic implants, sutures, profusion pumps, etc.

In accordance with the present invention, grafts of the thermoplastic substrates, such as silicone or Silastic ®, are cut into 0.5 cm segments and placed in a solution of an anionic surfactant, such as a 1% ethanol solution of dioctadecylphosphate for a period of time of from 5 to 120 minutes, preferably about 30 minutes, at a temperature of from 0 degrees to 55 degrees C, preferably at ambient temperature. The grafts are air dried and thoroughly washed in distilled water.

The grafts having an absorbed coating of dioctadecylphosphate are then placed in a drug, e.g. Tobramycin, Clindamycin or other antibiotic or like drug, agent or factor, for a period of time of from 5 to 120 minutes, preferably 60 minutes, at a temperature of from 0 degrees to 35 degrees C., preferably 25 degrees C. The thus treated grafts are then thoroughly washed, preferably in distilled water to remove loosely bound antibiotic material.

The devices coated with antibiotics as described above are suitable for all of the applications for which such devices are contemplated. The devices so prepared may optionally be further treated in accordance with parent application Serial No. 06/849,848 by the application of water-insoluble ion exchange resins. In some instances, this treatment further reduces thrombogenicity and may accordingly be useful when applied to devices placed in the vascular system. Further, this subsequent ion exchange treatment enhances the ratio of the antibiotic/surfactant and the rate of release.

The surfactant/antibiotic coating may be modified by treatment with commercially available beads of water-insoluble ion-exchange resins. To facilitate understanding of this treatment, the present invention will be described with reference to vascular prosthesis treated with dioctadecylphosphate and subsequently treated with anionic antibiotics such as gentamicin.

The grafts having bound dioctadecylphosphate/antibiotic compound are immersed in a slurry of a particulate anionic exchange compound, such as DEAE Sepharose, a cross-linked agarose having amino ethane groups ($-CH_2-CH_2-NH_3^+$) attached thereto, for a period of time of from 6 to 72 hours, preferably 20 hours, at a temperature of from 0 degrees to 35 degrees C., preferably 25 degrees C. The immobilizing anionic exchange compound is in the form of beads having a particle size distribution of from 40 to 120 microns and is commercially available in such particle size distribution. The thus treated grafts are then thoroughly washed in distilled water.

While Applicants do not wish to be bound by any theory of invention, it appears that at least with respect to the system comprising the anionic surfactant and the oppositely charged antibiotic, that the antibiotic is bound to the surfactant by an exchange of counter-ions, sodium being replaced with positively charged antibiotic. However, not all surfactant molecules participate in this ion exchange, and a portion of the surfactant retains sodium as counter-ion. Further, it appears that the anion exchange compound has a high affinity for bound dioctadecylphosphate which has not exchanged its sodium for a cationic antibiotic molecule; such molecules, not being shielded by a bound antibiotic molecule, are selectively removed and thus, the ion exchange treatment reduces any thrombotic effects exerted by the dioctadecylphosphate. Further, the surface of the prosthesis, at a microscopic level, is filamentous with ridges and deep recesses. The molecules of dioctadecylphosphate and antibiotic compound are relatively small and presumably bind uniformly on the exposed ridges and the interstices of the prosthesis surface.

The particles of the cationic exchange compound, such as DEAESepharose, is sterically unable to penetrate into the deep valleys and surfaces of the prosthesis. Thus, the dioctadecylphosphate and antibiotic molecules remain bonded in such recesses for a longer period of time. Thus, the foregoing treatment yields in such instance a surface which is less thrombogenic, yet contains a sequestered reservoir of an antibiotic compound, and exhibits a reduced tendency to cause blood platelet aggregation.

As hereinabove discussed, the beads of anionic surfactant (commercially available) are of a particle size distribution of from 40 to 120 microns.

In addition to DEAE-Sepharose, effective anionic exchange compounds include DEAE cellulose, Dowex-1-chloride, etc.

Binding of Surfactant and Antibiotic to Prostheses Constructed of Metals: The invention can also be applied to prostheses constructed of metals, such as orthopedic implants (e.g., artificial hips). To facilitate an understanding of this use of the invention, the invention will be described with reference to the treatment of metallic discs (18mm diam. x 2 mm thick).

Metallic discs (6.87 $cm^2$ surface area) fabricated of test materials (titanium, microstructured titanium, cobalt chromium alloy, and microstructured cobalt-chromium) are treated with dioctadecylphosphate and antibiotic (e.g., gentamicin) as described previously in this disclosure.

Numerous surfactant-drug combinations can be prepared according to the present invention. Table 1 gives representative combinations with various prosthetic substrate materials.

of $^{125}$I-tPA ($2\times10^3$ cpm/μg—tissue plasminogen activator supplied by Genentech, Inc., So. San Francisco, CA). The prostheses are then washed 5 times in distilled water, and air dried at room temperature. Retention of tPA to prostheses is determined by liquid scintillation counting. The results of the binding of the various prosthesis to tPA is set forth in Table 2, below.

TABLE 1
Representative Binding of Drugs by Surfactant-coated Prostheses

| Class of Surfactant (1) | Name of Surfactant | Class of Drug | Name of Drug (2) | Drug Bound (3) | Prosthesis Material |
|---|---|---|---|---|---|
| Quaternary ammonium | Tetradodecylammonium | Anionic antibiotic | Penicillin | 21.2 | PTFE |
| Quaternary ammonium | TDMAC | Anionic antibiotic | Penicillin | 515.9 | Dacron |
| Quaternary ammonium | TDMAC | Anionic antibiotic | Penicillin | 304.0 | Polyglactin suture |
| Quaternary ammonium | TDMAC | Neutral antibiotic | Tetracycline | 242.9 | PTFE |
| Quaternary ammonium | TDMAC | Anionic antibiotic | Cefoxitin | 596.3 | PTFE |
| Quaternary ammonium | TDMAC | Anionic anti-inflammatory | Prostaglandin El | 24.2 | PTFE |
| Quaternary ammonium | TDMAC | Anionic antibiotic | Penicillin | 132.2 | Titanium 6AL-4V |
| Quaternary ammonium | TDMAC | Anionic anticoagulant | Heparin | 94.2 | PTFE |
| Quaternary ammonium | TDMAC | Anionic antibiotic | Penicillin | 913.2 | PTFE |
| Quaternary ammonium | TDMAC | Anionic antibiotic | Penicillin | 248.8 | Microstructured cobalt-chrome |
| Quaternary ammonium | TDMAC | Anionic antibiotic | Penicillin | 41.0 | Gut |
| Quaternary ammonium | TDMAC | Anionic antibiotic | Penicillin | 181.0 | Silastic |
| Quaternary ammonium | TDMAC | Anionic anticoagulant | Heparin | 20.0 | Silastic |
| Quaternary ammonium | TDMAC | Anionic antibiotic | Penicillin | 202.0 | Polyester suture |
| Quaternary ammonium | TDMAC | Anionic antibiotic | Penicillin | 293.0 | Silk suture |
| Quaternary ammonium | TDMAC | Anionic antibiotic | Penicillin | 408.0 | Polypropylene |
| Quaternary ammonium | TDMAC | Anionic antibiotic | Cefoxitin | 379.9 | Dacron |
| Quaternary ammonium | TDMAC | Anionic antibiotic | Penicillin | 74.1 | Cobalt-chromium |
| Quaternary ammonium | TDMAC | Thrombolytic enzyme | Plasminogen activator (4) | 52.2 | PTFE |
| Quaternary ammonium | TDMAC | Anionic antibiotic | Cefoxitin | 492.0 | PTFE |
| Quaternary ammonium | TDMAC | Anionic anti-inflammatory | Indomethocin | 241.3 | PTFE |
| Quaternary ammonium | TDMAC | Anionic anti-inflammatory | Aspirin | 722.8 | PTFE |
| Quaternary ammonium | TDMAC | Anionic antibiotic | Penicillin | 341.6 | Microstructured titanium |
| Quaternary ammonium | Benzalkonium | Anionic antibiotic | Penicillin | 36.5 | PTFE |
| Quaternary ammonium | Benzalkonium | Anionic antibiotic | Penicillin | 8.5 | Dacron |
| Quaternary ammonium | Benzalkonium | Anionic antibiotic | Cefoxitin | 114.3 | PTFE |
| Quaternary ammonium | Benazlkonium | Anionic anticoagulant | Heparin | 46.9 | PTFE |
| Quaternary ammonium | Benzalkonium | Anionic antibiotic | Cefoxitin | 42.3 | Dacron |
| Phosphatidic der. | Phosphatidylserine | Cationic antibiotic | Clindamycin | 47.0 | Silicone |
| Phosphatidic der. | Phosphatidate | Cationic antibiotic | Tobramycin | 58.0 | Silastic |
| Phosphatidic der. | Bis-phosphatidate | Cationic antibiotic | Clindamycin | 48.0 | Silastic |
| Phosphatidic der. | Bis-phosphatidate | Cationic antibiotic | Tobramycin | 28.0 | Silastic |
| Phosphate ester | Dioctadecylphosphate | Cationic antibiotic | Tobramycin | 52.0 | Silastic |
| Phosphate ester | Dicetylphosphate | Cationic antibiotic | Tobramycin | 34.0 | silastic |

(1) Coated from 5% solution of ethanol or chloroform
(2) Determined using radioactive drug; prosthesis coated from 1% aqueous solution
(3) Binding expressed as micrograms bound per square centimeter of surface area
(4) Non-radioactive tissue plasminogen activator determined by radioimmune assay Additionally, the present invention is described utilizing commercially available thrombolytic agents using prostheses, such as polytetrafluoroethylene vascular grafts, woven Dacron vascular grafts and catheters fabricated from certain organosilicone polymers, such as Silastic ® polyolefins, such as polyethylene or polyurethane. To facilitate an understanding of the present invention, the present invention will be described with reference to the binding of tissue plasminogen activator (tPA) by treatment of vascular prostheses prepared from polytetrafluoroethylene, although it will be understood by those skilled in the art that the present invention relates to the treatment of any of the above materials for use as catheters, heart valves, orthopedic implants, sutures, profusion pumps, etc.

The prostheses are bound with surfactant by incubation at room temperature in a solution of surfactant dissolved in ethanol or ethanol/chloroform (1:1) at a concentration of 50 mg/ml. After 30 minutes, the prostheses are removed from the surfactant and allowed to air dry at room temperature. The surfactant-treated polymers are then incubated for approximately 30 minutes at room temperature in 1 ml of an aqueous solution TABLE 2
Binding of tPA to PTFE Coated with Surfactants Differing in charge and Chemical Structure

| Surfactant | ug $^{125}$I-tPA bound cm$^2$ prosthesis |
|---|---|
| Untreated | 0.09 |
| Cationic surfactants[1] | |
| Tridodecylmethylammonium chloride | 33 |
| Tetradodecylammonium bromide | 10.2 |
| Dihexadecyldimethylammonium chloride | 17.8 |
| Anionic surfactants[2] | |
| Phosphatidic acid | 11.5 |
| Phosphatidylserine | 5.0 |
| Zwitterionic surfactant[3] | |
| Phosphatidylcholine | 14.0 |
| Water-soluble compounds[1] | |
| Lysine | 2.5 |
| Polylysine | 7.0 |

Surface treatments used the following concentration of modifiers
[1]Cationic quaternary ammonium compounds and lysine derivatives a 50 mg/ml
[2]Anions at 10 mg/ml
[3]Phosphatidylcholine at 100 mg/ml.

Preferred surfactants for binding tPA are tridodecylmethylammonium chloride (TDMAC) and phosphatic acid.

Numerous modifications and variations of the present invention are possible in light of the above teachings and, theretofore, within the scope of the appended claims, the invention may be practiced otherwise than as particularly described.

What is claimed is:

1. A prosthesis for use in in vivo surgery having a coating, respectively, of an anionic surfactant and an oppositely charged drug bound to the surfactant.

2. The prosthesis as defined in claim 1 wherein said drug is selected from the group consisting of clindamycin, tobramycin, aminoglycoside, gentamycin, kanamycin and streptomycin.

3. The prosthesis as defined in claim 1 wherein said drug is an antithrombotic drug.

4. The prosthesis as defined in claim 1 wherein said drug is a thrombolytic enzyme.

5. The prosthesis as defined in claim 4 wherein said thrombolytic enzyme is tissue plasminogen activator.

6. The prosthesis as defined in claim 1 wherein said surfactant is a dioctadecylphosphate.

7. The prosthesis as defined in claim 1 wherein said prosthesis is a vascular graft.

8. A method for preparing a prosthesis for use in in vivo surgery, which comprises:
    (a) contacting said prosthesis with an anionic surfactant to coat said prosthesis with said surfactant;
    (b) contacting said prosthesis of step (a) with a solution of an oppositely charged drug; and optionally
    (c) contacting said prosthesis of step (b) with an appropriate ion exchange compound to remove unbound surfactant.

9. The method as defined in claim 8 wherein the prosthesis of step (a) is washed to remove excess surfactant prior to step (b).

10. The method as defined in claim 8 wherein said prosthesis of step (b) is washed to remove unbound drug compound prior to step (c).

11. The method as defined in claim 9 wherein said prosthesis of step (b) is washed to remove unbound drug compound prior to step (c).

12. The method as defined in claim 8 wherein said surfactant is a dioctadecylphosphate.

13. The method as defined in claim 8 wherein said drug is selected from the group consisting of clindamycin, tobramycin, aminoglycoside, gentamycin, kanamycin and streptomycin.

14. The method as defined in claim 8 wherein said drug is an antithrombotic drug.

15. The method as defined in claim 8 wherein said drug is a thrombolytic enzyme.

16. The method as defined in claim 15 wherein said thrombolytic enzyme is tissue plasminogen activator.

17. The method as defined in claim 8 wherein said ion exchange compound is selected from the group consisting of DEAE-Sepharose—and DEAE-cellulose.

* * * * *